United States Patent [19]

Young

[11] 4,094,608

[45] June 13, 1978

[54] SPECTROMETER OF THE ELECTRO-OPTO-ACOUSTIC TYPE WITH CAPACITOR-TYPE DETECTION

[75] Inventor: Robert A. Young, Chatsworth, Calif.

[73] Assignee: Xonics, Inc., Van Nuys, Calif.

[21] Appl. No.: 732,309

[22] Filed: Oct. 14, 1976

[51] Int. Cl.² .................. G01J 3/42; G01N 21/06; G01R 27/26

[52] U.S. Cl. ........................... 356/97; 73/24; 324/61 R; 356/201; 356/204; 356/205; 361/280

[58] Field of Search ............... 356/97, 201, 204, 205, 356/206; 324/61 R; 361/280, 281, 282; 73/24, 26

[56] References Cited

U.S. PATENT DOCUMENTS

| 2,870,338 | 1/1959 | Gillson, Jr. ............... 361/281 |
| 3,493,484 | 2/1970 | Berg et al. ............... 324/61 R |

Primary Examiner—Vincent P. McGraw
Attorney, Agent, or Firm—Harris, Kern, Wallen & Tinsley

[57] ABSTRACT

A spectrometer generally of the electro-opto-acoustic type, using a capacitor type detection instead of acoustic detection. A holder with a sample carrier having a dielectric and with a conducting backing plate on one surface of the sample carrier and a transparent conducting coating and an electrical potential on the opposite surface, with the potential applied after sample accumulation. A source for directing a beam of radiation onto the sample for cyclically heating the sample and varying the spacing between the metal backing plate and conducting coating, and an ac detector circuit connected to the backing plate providing an ac signal varying with the spacing and hence with the composition of the sample.

35 Claims, 9 Drawing Figures

SPECTROMETER OF THE ELECTRO-OPTO-ACOUSTIC TYPE WITH CAPACITOR-TYPE DETECTION

BACKGROUND OF THE INVENTION

This invention relates to sample analysis and in particular to a new and improved spectrometer of the electro-opto-acoustic type, using capacitative rather than acoustic detection.

Recently, several methods have been developed to measure heat which is generated in gases, liquids and solids by the absorption of light energy. This energy is characteristic of resonantly absorbed light which, in turn, is characteristic of the type and number of atoms and molecules which are responsible for the absorption. Other processes which scatter light are not detected.

This method of measuring which provides a measure of the amount of atoms or molecules in the absorbing medium, has great practical advantages over simply measuring the amount of light removed from a collimated light beam because, when this amount is small, great precision of measurement and great stability of light source and detector are required.

Light scattered from the beam may be measured to provide a measure of the composition of the scattering material. However, this method is not satisfactory in many instances because the scattering will be due to many processes not specifically characteristic of the constituents of the sample (surface scattering, Rayleigh scattering, particulate scattering, etc.). Under many conditions, the resonantly absorbed light is not re-radiated, because the resonant process is the slowest to radiate of all those processes absorbing radiation. The amount of light scattered by this process is thus greatly reduced. Furthermore, resonantly scattered light is extremely difficult to separate from light scattered by other processes.

The heat deposited in a confined gas sample by resonant absorption causes its temperature to rise and this increases its pressure. If the gas sample is periodically illuminated, the oscillating pressure constitutes a sound wave which can be measured with a microphone. This effect has been used with both laser and non-laser light sources to measure the light energy resonantly absorbed by gases and solids in energy contact with a confined gas. Examples of and apparatus for this process are set forth in U.S. Pat. Nos. 3,820,901, 3,659,452, 3,893,771, and 3,911,276, and reference may be had to these patents for more details on the electro-opto-acoustic spectrometer.

It is an object of the present invention to provide for sample collection in a sample carrier at one location and analysis of the sample in a spectrometer at another location. It is a further object of the invention to provide method and apparatus for sample analysis wherein radiant energy is absorbed by a sample resulting in heating and expansion of the sample, with the expansion in a capacitor environment providing an ac signal which can be related to the composition of the sample.

SUMMARY OF THE INVENTION

In the method of the invention, a sample is collected in a sample carrier with a conducting backing sheet provided for one surface of the sample carrier and after the sample is collected, a conducting transparent layer with an electrical potential is provided on the opposite surface of the sample carrier. A beam of radiation is directed onto the sample cyclically heating the sample causing it to expand and contract and thereby vary the spacing between the electrical potential and the backing sheet. The sample carrier with collected sample between the backing sheet and the charged conducting layer functions as a capacitor and the varying spacing between the capacitor plates produces an ac signal which may be amplified and demodulated to provide a measure of the composition of the sample.

The apparatus of the invention includes a holder with conducting backing sheet, a sample carrier, a conducting layer on the carrier and an electrical potential on the layer, a source providing a beam of radiation directed onto the carrier and modulated or cyclically deflected, and an ac detection circuit coupled to the conducting backing sheet and providing an output varying as a function of the composition of the sample carrier with the sample thereat.

The electrical potential on the conducting layer may be provided by connection to a dc source or by generation of a plurality of electrostatic charges. The backing sheet may be segmented providing two capacitors, and the radiation beam may be modulated or deflected to provide the ac output.

DESCRIPTION OF THE PREFERRED EMBODIMENTS

Figures 1, 2:
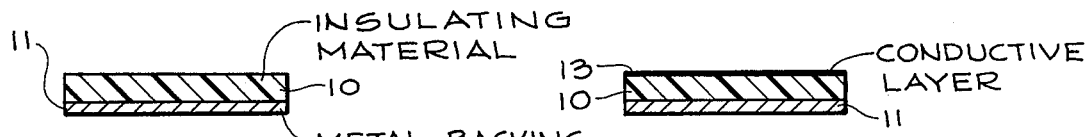
FIG. 1 is a section view through a holder suitable for collecting a sample.
FIG. 2 is a view of the holder of FIG. 1 after sample collection and provision of a conducting layer, with the holder ready for analysis.

One form of holder suitable for use with the invention is illustrated in FIG. 1. A layer 10 of an electrical insulating material is carried on an electrically conducting backing sheet 11, typically a thin metal sheet. The layer 10 functions as a sample carrier, with a sample being absorbed on its surface or dissolved or embedded in the material. The sample is collected by placing the holder in the environment from which it is desired to obtain the sample or by actively passing a fluid over or through the surface.

By way of example, polystyrene which absorbs the monomers of several plastics, can be used as the insulating layer 10. Pyridine benzene copolymers and amine - copolymers (such as 4 vinyl pyridine divinyl-benzene) are suitable for use as the insulating layer 10 for absorbing $SO_2$. The materials identified may be utilized in the form of solid sheets, fibers, cloth, fabric, gels, powder or liquids.

Figure 3:
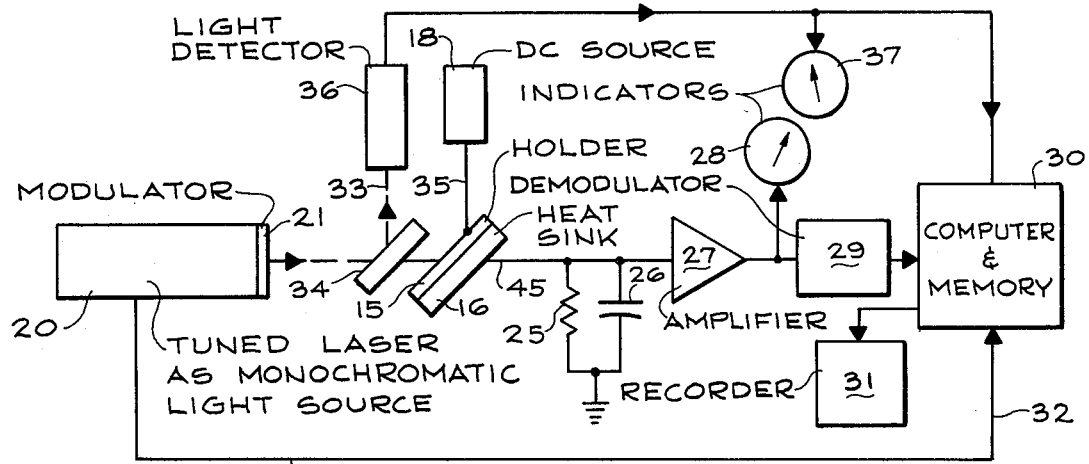
FIG. 3 is a diagram of a spectrometer incorporating one embodiment of the invention.

After sample collection, the holder is treated and is then ready for insertion into the spectrometer of FIG. 3. A thin layer 13 of a transparent electrical conductive material is applied onto the sample carrier. The conductive layer can be water containing a dissolved salt or weak acid. An electrical potential is provided on the conducting layer 13. In one embodiment, a layer of electrostatic charges 12 is formed on the sample carrier, typically by a conventional corona discharge device or by ultraviolet radiation. In another embodiment, the electrical potential is obtained by connecting the layer 13 to a dc source, such as the source 18 of FIG. 3. The applied voltage may be in the range of 100 volts to 10 kv, typically about 1 kv.

The holder of FIG. 2, identified by reference numeral 15, is positioned in the spectrometer of FIG. 3. The holder 15 preferably is mounted on a larger metal block 16 which serves as a heatsink, with the metal backing sheet 11 contacting the block 16. A modulated beam 17 of radiation is directed onto the sample carrier. Preferably, the radiation is substantially monochromatic and in the embodiment illustrated, a tuned laser 20 is used as the source. The laser output is modulated by a modulator 21 which may typically be a beam chopper for amplitude modulation or a laser cavity tuner for wavelength modulation.

A detector circuit is connected to the backing sheet 11 via the heatsink 16 and typically comprises a resistor 25 connected in parallel with a capacitor 26 between the sheet 11 and circuit ground. An amplifier 27 provides an output to an indicator 28 and a demodulator 29. The demodulator output may be coupled to a computer and/or a memory indicated at 30 and it may be recorded directly in a recorder 31. The laser 20 may be connected to the computer 30 via line 32 to provide data on laser tuning to the computer.

Also, radiation of the beam 17 may be scattered along path 33 by a beam splitter 34 and detected in a light detector 36, with the detector output connected to another indicator 37 and/or directly as an input to the computer 30. This provides a measure of the laser output power.

With the sample carrier in position and the radiation source modulated, radiation is periodically absorbed in the sample carrier causing it to heat and periodically expand and contract, thus periodically changing the separation between the backing sheet 11 and the conducting layer 13. This produces a periodic or ac signal which may be amplified, demodulated, measured and/or further processed for storage or display. In the simpler system, the demodulator output is merely displayed or recorded. In the more complex systems, the demodulator output may be used in conjunction with inputs from the laser indicating radiation frequency and from the light detector indicating laser output power to provide a more sophisticated analysis of the sample. In any event, the ac signal from the holder during radiation by the modulated beam provides a measure of the composition of the sample in the sample carrier.

For small absorption the energy absorbed $E_a$ at wavelength $\lambda$ is given by $$E_a(\lambda) = E_i(\lambda) \sum_{j=1}^{m} \sigma_j(\lambda) N_j$$

where $\sigma_j(\lambda)$ is the cross section for absorption at $\lambda$ of species $j$ with number density $N_j$. The incident energy $E_i(\lambda)$ is proportional to the signal received by light detector 36 whose output is $S_i$. If the output of the demodulator 24 is $S_a$ which is proportional to $E_a(\lambda)$ then $$\frac{S_a}{S_i} = K(\lambda) \sum_{j=1}^{m} \sigma_j(\lambda) N_j$$

If the apparatus has been previously calibrated by inserting samples for which $$\sum_{j=1}^{m} \sigma_j(\lambda) N_j$$

is known so that $K(\lambda)$ can be determined, the value of $S_a/S_i$ measured gives $$\sum_{j=1}^{m} \sigma_j(\lambda) N_j = C(\lambda)$$

If similar measurements are made at a set of wavelength $\lambda\mu$ a set of linear equations results $$\sum_{j=1}^{m} \sigma_j(\lambda\mu) N_j = C(\lambda\mu), \mu = 1 \text{ to } n$$

If $n \leq m$ this set of equations can easily be solved to give $N_j$ for $j=1$ to $m$. Thus the composition of the unknown sample, i.e., the set $N_j$, are measured.

To take account of any overall drift of the system the sample carrier can be impregnated with a known concentration of a known calibration specie Ng to normalize the instrument response.

Figure 4:
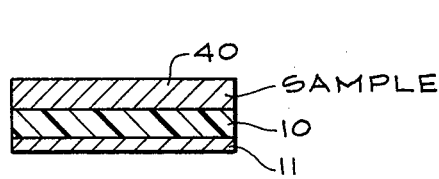
FIGS. 4 and 5 are views similar to that of FIG. 1 showing alternative embodiments of the holder.

Some alternative configurations for the holder are shown in FIGS. 4–7. In the embodiment of FIG. 4, a sample layer 40 may be adhered or affixed to the insulating sheet 10, permitting the sample to take any form that can be attached to the insulating sheet. The sample 40 need not be electrically insulating. It can be solid, a gel, or a liquid film, and its texture can be smooth or rough. It can be in the form of filaments, matted or woven, or particles of material, or drops of gel or liquid, or any combination of these.

By way of example, the layer 10 may be formed from Teflon, PVC, polystyrene or mylar, and the layer 40 may be composed of either silica gel modified with amine hydrobromide for measurement of $SO_2$ or modified with O - Tolidine chloride, antipyrine, or dimethylailine for measurement of $NO_2$, or filter paper with tetramethyl-p-diamidodiphenyl-amine, bensidine, thallnium hydroxide, or 4, 4' tetramethyldiamino diphenylamine for measurement of ozone.

In addition, the layer 10 or 40 may contain a material which changes color or becomes colored when exposed to the sample, with the amount of color change or colored material generated being a measure of the concentration of a species in the sample. For example, the layer 10 could be mylar and the layer 40 silica gel impregnated with sodium tetrachloromecurate for $SO_2$ measurement or potassium permanganate for $NO_2$ measurement.

Figure 5:
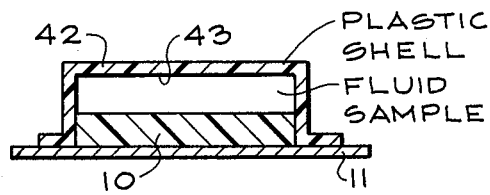

In the embodiment of FIG. 5, a shell or cap 42, typically of plastic, is carried on the metal sheet 11, defining a sample space 43. The cap 42 should be substantially transparent at the wavelength of the radiation source. Any type of solid or fluid sample or sample carrier can be positioned in the space 43.

Figure 6:
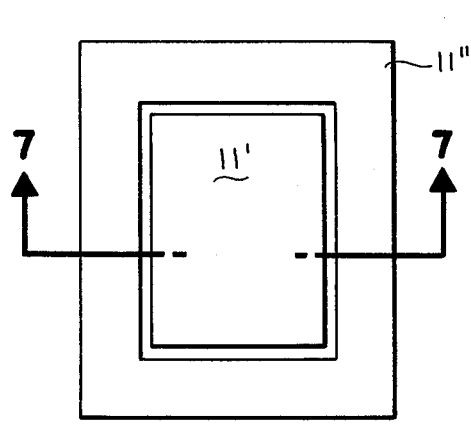
FIG. 6 is a plan view of another alternative embodiment of the holder.
Figure 7:
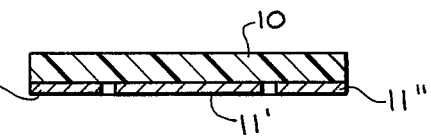
FIG. 7 is a sectional view taken along the line 7—7 of FIG. 6.

In the embodiment of FIGS. 6 and 7, the conducting backing sheet is formed in two sections 11' and 11" electrically insulated from each other. The smaller inner section 11' may be mounted on the heatsink 16 and connected to the detector circuit via line 45. The larger outer section 11" may rest on another metal plate 16' which is connected to circuit ground and which also serves as a heatsink.

Figure 8:
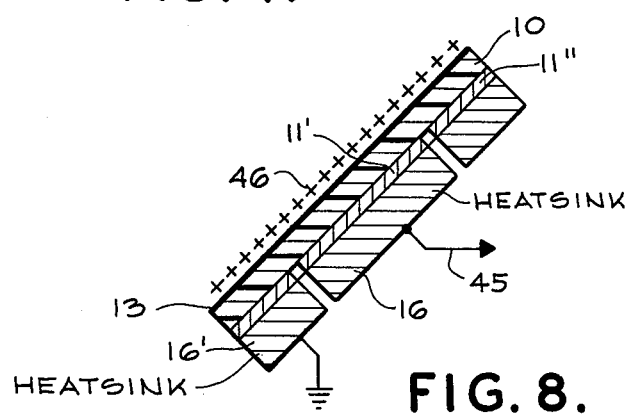
FIG. 8 is a view illustrating the holder of FIG. 7 as mounted on a spectrometer.

The holder of FIGS. 6-8 may be used in the spectrometer of FIG. 3 with the dc source 18 connected to the conducting layer 13. Alternatively, a plurality of electrostatic charges 46 may be produced on the layer 13 prior to inserting the holder into the spectrometer, in the manner discussed previously, and the dc source 18 may be omitted.

Figure 9:
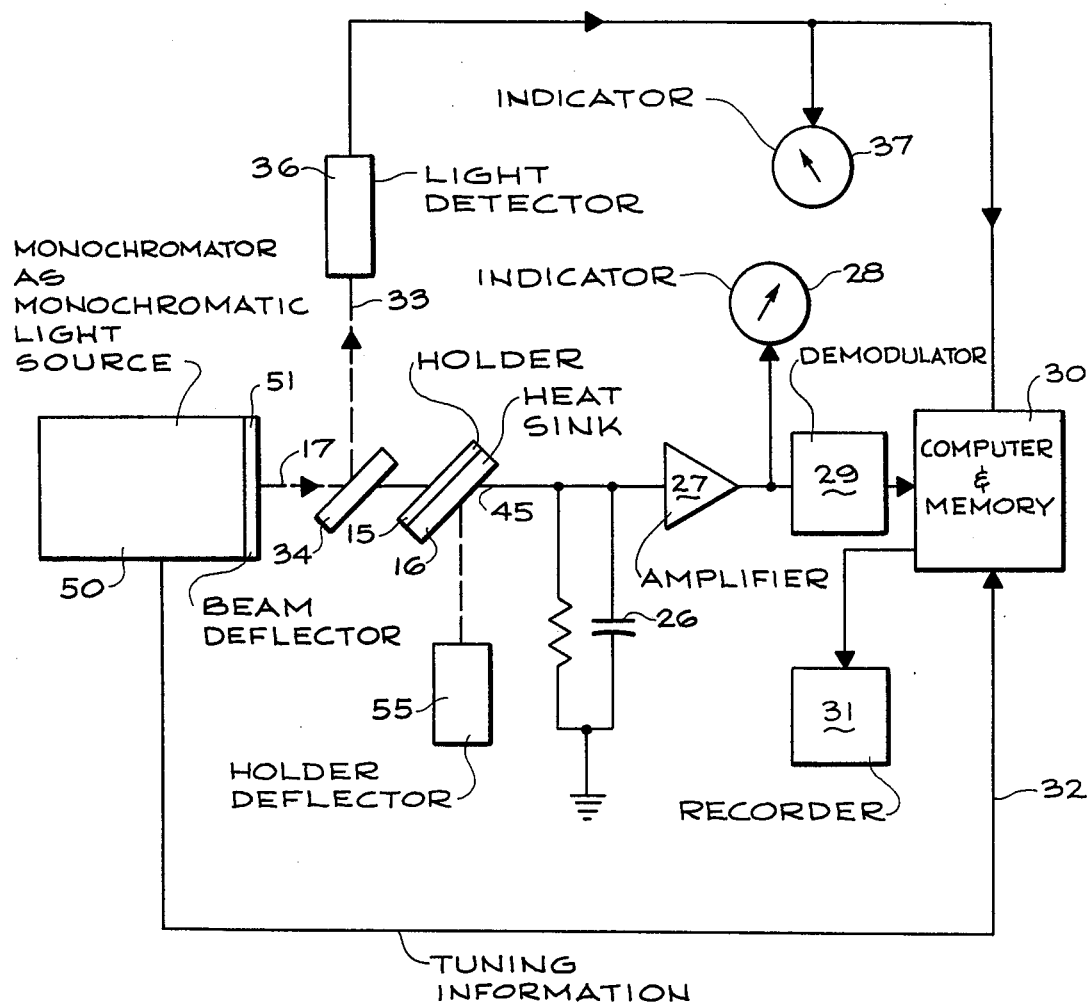
FIG. 9 is a diagram similar to that of FIG. 3 showing an alternative and presently preferred embodiment of the invention, using the holder of FIGS. 6-8.

A number of other variations of the invention are illustrated in FIG. 9, where elements corresponding to those of FIG. 3 are identified by the same reference numerals. The dc source 18 is omitted, and the electrical potential on the conducting layer 13 will be provided by the electrostatic charges 46. A monochromator 50 is used in place of the laser 20 to provide the radiation beam. A monochromator will provide a relatively narrow band of radiation, typically in the order of about one angstrom. A beam deflector 51 is utilized in place of the modulator 21. In one mode of operation, only a portion of the sample carrier is exposed to the sample during the sampling procedure so that one portion of the sample carrier does not receive any sample material. By way of example, a mask corresponding to the section 11' may be placed over the sample carrier so that only the center portion corresponding to the section 11' collects sample. Then when the holder is positioned in the spectrometer, the beam is moved cyclically between a position directed to the section 11' and a position directed to the section 11". Alternatively, the beam can remain stationary and the holder can be moved by means of a holder deflector 55. Of course, the portion of the sample carrier exposed to the sample does not have to correspond in shape or size to a segment of the segmented backing. Also, it will be noted that a segmented backing plate is not necessary and that a continuous backing plate such as is shown in FIG. 1 can be utilized with a portion of the sample carrier protected from the sample. Also, it will be noted that the variations of FIG. 9 are not limited to use with each other, by way of example, the monochromator of FIG. 9 can be used in the system of FIG. 3 and the laser of FIG. 3 can be used in the system of FIG. 9.

I claim:

1. In a spectrometer, the combination of:
   a holder having a conducting sheet with a sample carrier including an electrical insulator on said conducting sheet, a conducting layer on the surface of said sample carrier spaced from said sheet, and an electrical potential on said conducting layer;
   a radiation source providing a beam of radiation directed onto said sample carrier; and
   an ac detector circuit connected to said conducting sheet and providing an output varying as a function of the condition of said sample carrier.

2. The apparatus as defined in claim 1 wherein said electrical potential is provided by a dc source connected to said conducting layer.

3. The apparatus as defined in claim 1 wherein said electrical potential is provided by a plurality of electrostatic charges at said conducting layer.

4. The apparatus as defined in claim 3 wherein said conducting sheet of said holder is in two separate pieces electrically insulated from each other, with one piece connected to said ac detector circuit and the other piece connected to circuit ground.

5. The apparatus as defined in claim 1 including a heatsink, with said holder carried on said heatsink with said conducting sheet in engagement with said heatsink.

6. The apparatus as defined in claim 1 wherein said detector circuit includes a resistor and a capacitor connected in parallel between said conducting sheet and circuit ground, and an amplifier having its input connected to said conducting sheet.

7. The apparatus as defined in claim 6 wherein said detector circuit further includes a demodulator having the amplifier output connected as an input and providing a demodulated output signal for storage and/or recording.

8. The apparatus as defined in claim 1 including a beam splitter and a radiation detector positioned to receive radiation from said source scattered by said beam splitter.

9. The apparatus as defined in claim 8 including a computer having the radiation detector output and the ac detector circuit output as inputs.

10. The apparatus as defined in claim 1 including modulation means for modulating said beam of radiation.

11. The apparatus as defined in claim 1 including means for moving said beam relative to said holder for deflecting the beam across the sample carrier.

12. The apparatus as defined in claim 1 wherein the sample is carried in said electrical insulator on said conducting sheet of said holder.

13. The apparatus as defined in claim 1 wherein the sample is carried in a layer attached to said electrical insulator on said conducting sheet of said holder.

14. The apparatus as defined in claim 1 wherein said holder includes a retainer shell carried on said conducting sheet and defining a sample space over said electrical insulator.

15. The apparatus as defined in claim 1 wherein said sample carrier includes a material which reacts with a sample to produce a change in color of the sample carrier.

16. The apparatus as defined in claim 1 wherein said conducting sheet of said holder is in two separate pieces electrically insulated from each other, with one piece connected to said ac detector circuit and the other piece connected to circuit ground.

17. The apparatus as defined in claim 1 wherein a first portion of said sample carrier has been exposed to a sample and a second portion of said sample carrier has not been exposed to the sample, and including means for moving said beam relative to said holder for cyclically deflecting the beam onto said first and second portions.

18. The apparatus as defined in claim 17 including a known amount of a known constituent in said second portion for purposes of instrument calibration.

19. The apparatus as defined in claim 17 wherein said conducting sheet of said holder is in two separate pieces electrically insulated from each other, with one piece connected to said ac detector circuit and the other piece connected to circuit ground, and with said first portion of said sample carrier overlying one piece of said sheet and said second portion overlying the other piece.

20. The apparatus as defined in claim 1 including a known amount of a known constituent in said sample carrier for purposes of instrument calibration.

21. The apparatus as defined in claim 1 wherein said radiation source includes a laser.

22. The apparatus as defined in claim 1 wherein said radiation source includes a monochromator.

23. A method of analyzing a sample including the steps of:
 collecting the sample in a sample carrier;
 providing a conducting backing sheet for one surface of the sample carrier;
 after collection of the sample providing an electrical potential on a conducting layer at the opposite surface of the sample carrier;
 directing a beam of radiation onto the sample to cyclically heat the sample and vary the spacing between the electrical potential and the backing sheet; and
 producing an ac signal varying with the variation in spacing.

24. The method as defined in claim 23 including sensing radiation of the beam scattered by an element in the beam, and producing another signal varying with the intensity of the scattering.

25. The method as defined in claim 23 including producing the beam of radiation with a monochromator.

26. The method as defined in claim 23 including producing the beam of radiation with a substantially monochromatic laser.

27. The method as defined in claim 23 including amplitude modulating the beam of radiation.

28. The method as defined in claim 23 including wavelength modulating the beam of radiation.

29. The method as defined in claim 23 including cyclically moving the beam relative to the carrier.

30. The method as defined in claim 23 including collecting the sample in only a first portion of the sample carrier, and cyclically deflecting the beam of radiation onto the first portion and a second portion of the carrier.

31. The method as defined in claim 30 including introducing a known amount of a known constituent in the second portion of the sample carrier for purposes of instrument calibration.

32. The method as defined in claim 23 including introducing a known amount of a known constituent in the sample carrier for purposes of instrument calibration.

33. The method as defined in claim 23 including producing the electrical potential at the sample carrier by exposure to a source of positive electrostatic charges.

34. The method as defined in claim 23 including producing the electrical potential at the sample carrier by connecting the conducting layer to a dc source.

35. The method as defined in claim 23 wherein the sample is collected in a material which reacts with the sample to produce a change in color.

* * * * *